(12) United States Patent
Van De Waal et al.

(10) Patent No.: US 7,008,919 B2
(45) Date of Patent: Mar. 7, 2006

(54) USE OF THIO DERIVATIVES AS PERFUMING AND FLAVORING INGREDIENTS

(75) Inventors: Matthijs Van De Waal, Laconnex (CH); Sina Dorothea Escher, Confignon (CH); Yvan Niclass, Grand-Saconnex (CH)

(73) Assignee: Firmenich SA, Geneva (CH)

( * ) Notice: Subject to any disclaimer, the term of this patent is extended or adjusted under 35 U.S.C. 154(b) by 443 days.

(21) Appl. No.: 10/106,541

(22) Filed: Mar. 25, 2002

(65) Prior Publication Data

US 2003/0040460 A1 Feb. 27, 2003

(30) Foreign Application Priority Data

Apr. 12, 2001 (WO) .................. PCT/IB01/00631

(51) Int. Cl.
*A61K 7/46* (2006.01)
(52) U.S. Cl. .................. 512/7; 426/535; 426/650; 549/90; 549/554; 558/252; 558/62
(58) Field of Classification Search .................. 512/7; 426/535, 650; 549/90, 554; 558/252, 62
See application file for complete search history.

(56) References Cited

U.S. PATENT DOCUMENTS 6,129,941 A 10/2000 Escher et al. ............... 426/535

FOREIGN PATENT DOCUMENTS

EP 0 982 295 A2 3/2000

OTHER PUBLICATIONS

Van de Waal et al. "1-Methoxyhexane-3-thiol, a Powerful Odorant of Clary Sage", Helvetica Chimica Acta, vol. 85, 1246-1260, 2002.*
Zibeth, XP-002100630, "Fenaroli's Handbook of Flavor Ingredients Natural Flavors", pp. 327-328, (1992).
Engel et al., "Identification of new sulfur-containing volatiles in yellow passion fruits (*Passilflora edulis* f. flavicarps)" Journal of Agricultural and Food Chemistry, vol. 39, No. 12, pp. 2249-2252 (1991).

* cited by examiner

*Primary Examiner*—Monique T. Cole
(74) *Attorney, Agent, or Firm*—Winston & Strawn LLP

(57) ABSTRACT

The compounds of formula

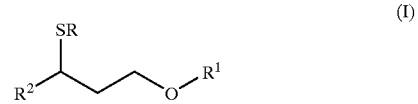

(I)

in the form of any one of their isomers or of mixtures thereof, and wherein R represents a hydrogen atom or an acetyl group, $R^1$ represents a methyl or an ethyl group and $R^2$ represents a $C_3$–$C_4$ linear or branched alkyl group, are useful for the perfume and flavor industries.

7 Claims, No Drawings

USE OF THIO DERIVATIVES AS PERFUMING AND FLAVORING INGREDIENTS

TECHNICAL FIELD

The present invention relates to the perfume and flavor industries. It concerns more particularly a compound of formula

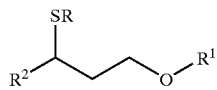

in the form of any one of its isomers or of a mixture thereof, and wherein R represents a hydrogen atom or an acetyl group, $R^1$ represents a methyl or an ethyl group and $R^2$ represents a $C_3$–$C_4$ linear or branched alkyl group. The invention concerns also the use of such a compound as a perfuming or flavoring ingredient.

PRIOR ART

To the best of our knowledge, there is only one prior art document describing compounds which are encompassed by formula (I).

EP 0 982 295 teaches the use as perfuming or flavor ingredients of compounds of formula

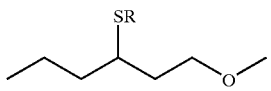

wherein R represents a hydrogen atom or an acetyl group.

The compounds of formula (II) are described as being able to confer an odor effect extremely powerful of the clary-sage type, even when used in small amounts. The taste conferred by said compounds is of the exotic fruit type with a mint note.

Amongst the compounds of formula (A), S-[1-(2-methoxyethyl)butyl] ethanethioate is said to possess an odor with a typical sulfury note, accompanied by box-tree (Buxus), blackcurrant and onion type notes, which odor is also reminiscent of the odor of sage.

As for 1-methoxy-3-hexanethiol, which also obeys formula (A), it is said to develop an odor of the sulfury type, but its fragrance also presents very natural green and herbaceous odor notes, which can be described as being reminiscent of the odor of the clary-sage. Its flavor, in addition to the above mentioned exotic fruit-minty effect, is described as being also reminiscent of grapefruit.

This document is however totally silent as to the possible usefulness of any compounds structurally similar to compounds (A).

DESCRIPTION OF THE INVENTION

Surprisingly, we have now been able to establish that the compounds of formula

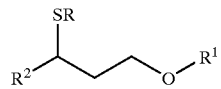

in the form of any one of their possible isomers or of mixtures thereof, and wherein R represents a hydrogen atom or an acetyl group, $R^1$ represents a methyl or an ethyl group and $R^2$ represents a $C_3$–$C_4$ linear or branched alkyl group, possess useful organoleptic properties, which render them very useful for the perfume and flavor industries.

As hereinabove anticipated, the compounds of formula (I) may also be in an optically active form as they possess at least one chiral centre, i.e. the carbon atom bearing the $R^2$ group and the sulfur atom.

The organoleptic properties of the isomers can differ from those of the respective racemates and in some cases, the pure optically active isomers possessed preferred organoleptic properties when compared with the respective racemates or even optically active mixtures of chiral isomers.

More particularly, the compounds (I) possess very natural and powerful sulfury green, herbaceous odors and are able to impart to the compositions to which they are added typical and surprising fruity tonalities.

Thus, the compounds (I) provide typical and well-marked odor effects, when said compounds are incorporated in perfumes, even at high dilutions. Furthermore, although compounds (I) all seem to be characterized by their typical sulfury, green notes, a variety of odor nuances can be found amongst the various compounds of formula (I). For example, 1-methoxyheptane-3-thiol imparts a floral, green gardenia note recalling the floral-fruity odor of styrallyl acetate, whereas 1-ethoxyhexane-3-thiol is able to impart a berry, blackberry type and vegetable note.

As for 1-methoxy-4-methylpentane-3-thiol, it is particularly appreciated by the perfumers and is therefore a preferred ingredient of the invention. This compound develops an odor of the sulfury, herbaceous type and additionally it is able to impart to a composition a very much appreciated and marked fruity tonality, which is quite unexpected in view of the above-cited prior art disclosure.

As optically active compounds one can cite the (S)-1-methoxyheptane-3-thiol which has a nice natural blackcurrant note accompanied by green and tropical fruit notes.

The compounds of formula (I) wherein R represents an acetyl group, in addition to their typical sulfury, green notes, have also typical tropical fruity notes. In particular S-[1-(2-ethoxyethyl)pentyl] ethanethioate and S-[1-(2-ethoxyethyl)butyl] ethanethioate develop, respectively, a grapefruit and a herbaceous note.

The odor properties of the compounds of the invention, and the odor effects they can provide to the compositions in which they are incorporated, thus appear as totally unexpected in view of the prior art, which is totally silent with regard to these compounds and their typical odor.

The ethers of the invention can suit almost all the fields of modem perfumery. One can cite the applications in fine perfumery, namely in the creation of perfumes and colognes wherein novel and original odor effects can be obtained.

The compounds (I) can also be used in functional perfumery, namely to perfume soaps, shower or bath gels, shampoos, body deodorants and antiperspirants, ambient air deodorants, liquid or solid detergents for textile treatment, detergent compositions or cleaning products for dishes or varied surfaces, or cosmetic preparations.

In these applications, the compounds according to the invention can be used alone, as well as mixed with other perfuming ingredients, solvents or additives commonly used in perfumery. The nature and variety of these coingredients do not require a more detailed description here, which would not be exhaustive anyway. In fact, a person skilled in the art, having a general knowledge, is able to choose them according to the nature of the product that has to be perfumed and the olfactory effect sought. These perfuming coingredients belong to varied chemical groups such as alcohols, aldehydes, ketones, esters, ethers, acetates, nitriles, terpernic hydrocarbons, heterocyclic nitrogen- or sulfur-containing compounds, as well as natural or synthetic essential oils. Many of these ingredients are listed in reference texts such as S. Arctander, Perfume and Flavor Chemicals, 1969, Montclair, N.J., USA, or more recent versions thereof, or in other similar books, as well as in the abundant patent literature in the art of perfumery.

As is usual in perfumery, the choice of such co-ingredients shall also be dictated by the particular use to which the end-product is destined and the perfumer will select such materials accordingly in order to ensure maximum performance from the fragrance, hedonically and over a period of time, upon use of the end-product.

The proportions in which the compounds according to the invention can be incorporated in the different products mentioned above vary in a broad range of values. These values depend on the nature of the product that has to be perfumed and on the olfactory effect sought, as well as on the nature of the coingredients in a given composition when the compounds of the invention are used in admixture with perfuming coingredients, solvents or additives commonly used in the art.

In a general manner, the compounds according to the invention will be used in small amounts, typically at very high dilutions, owing to their strong odor impact.

For instance, concentrations from 1 ppm to 1%, and preferably from 10 ppm to 0.1% by weight of these compounds, with respect to the weight of the perfuming composition in which they are incorporated, can typically be used. Much lower concentrations than these can be used when these compounds are directly applied for perfuming some of the consumer products mentioned above.

As anticipated above, the compounds of formula (I) are also useful as flavoring ingredients, i.e. to impart taste to flavoring compositions and foods, pharmaceuticals or beverages for example. Their taste is associated with tropical fruits and berries notes. For example, (R)-1-methoxy-4-methylpentane-3-thiol imparts an unexpected black-currant and guava flavor note.

As for (S)-1-methoxyheptane-3-thiol, which is particularly appreciated and is therefore a preferred flavor ingredient of the invention, in addition to its guava and passion fruit notes, also provides a very good and surprising berry note, including tonalities of the blackcurrant, strawberry, raspberry or blackberry type.

The compounds of the invention are thus particularly suitable for the flavoring of products such as desserts, ice-creams, candies, beverages such as sodas or juices, compotes or fruit jams, yogurts or other dairy products, chewing-gums, pharmaceutical preparations, soups or stocks, cube stocks, dressings, snacks, sauces or ready cooked dishes.

In these applications the compounds according to the invention will typically be used in concentrations of the order of 0.001 to 0.1 ppm, preferably from 0.01 to 0.05 ppm, with respect to the foods into which they are incorporated. Much higher concentrations can be used when these compounds are directly applied in concentrated flavor or flavoring compositions which will be incorporated in consumer products.

Amongst the compounds of formula (I), the thiols are the preferred perfuming or flavoring ingredients of the invention.

The compounds (I) of the invention thus make it possible to confer, improve, enhance or modify the odor or taste of consumer products, as well as of perfuming bases or concentrates, or yet flavor preparations and compositions. In other words, they can impart to the latter their characteristic organoleptic properties, as the case may be, thus modifying and/or improving the original odor and taste properties of the products and compositions in which they are incorporated.

The invention will be now described in greater detail in the following examples, wherein the abbreviations have the usual meaning in the art, the temperatures are indicated in degrees centigrade (° C.); the NMR spectral data were recorded on a Bruker-AMX-360 spectrometer and the chemical displacement δ are indicated in ppm with respect to the TMS as standard; the IR spectra are given in $cm^{-1}$.

Commercially available reagents and solvents of adequate quality were used without further purification and the reactions were carried out under Ar.

EXAMPLE 1

Synthesis of the Racemic Compounds of the Invention

The compounds of the invention may be prepared by the method summarized in the following scheme (I):

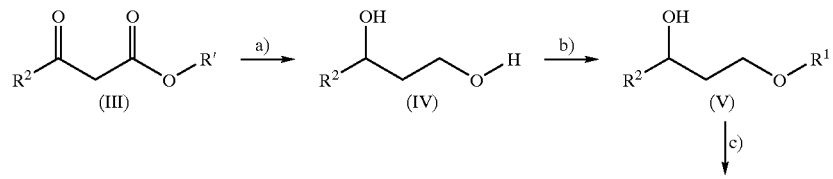

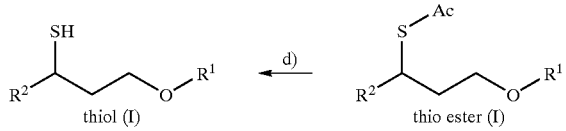

a) 1) NaBH$_4$/EtOH;
   2) LiAlH$_4$/Et$_2$O
b) KH/R$^1$I/THF
c) 1,3-dimethyl-2-fluoropyridinium tosylate/NEt$_3$/AcSH/acetone/C$_6$H$_6$
d) LiAlH$_4$/Et$_2$O
Ac = CH$_3$C(O)——
R$^1$ and R$^2$ as defined above
R' being a C$_{1-4}$ alkyl group a) General Procedure for the Preparation of Intermediates (IV)

To a mixture of NaBH$_4$ (4.08 g, 107 mmol) in EtOH (350 ml), the starting compound (III) (structure according to Table 1, 300 mmol) in EtOH (300 ml) was added dropwise at 5–10°. After stirring at room temperature overnight, GC analysis showed absence of the starting material. EtOH was removed at reduced pressure. The crude product in anhydrous Et$_2$O (300 ml) was added to an ice-cooled suspension of LiAlH$_4$ (11.4 g, 300 mmol) in Et$_2$O (800 ml). After one night at room temperature, the suspension was cooled to 5° and carefully hydrolyzed by consecutive addition of H$_2$O (11.4 ml), 15% NaOH solution (11.4 ml), and H$_2$O (34.2 ml). After 1 h stirring at room temperature, Na$_2$SO$_4$ was added, and the whole was filtered. The filtrate was concentrated, and the residue was distilled (Vigreux column) to afford the diol intermediates (IV).

TABLE 1

| R$^2$ | R' | Final Product | Yield |
|---|---|---|---|
| $^n$Pr | Et | Hexane-1,3-diol | 75% |
| $^n$Bu | Me | Heptane-1,3-diol | 76% |
| $^i$Pr | Me | 4-Methylpentane-1,3-diol | 73% |

Hexane-1,3-diol

B.p. 80–82°/2 mbar.

$^1$H-NMR (after exchange with D$_2$O): 3.90–3.75(m, 1H—C(3), 2H—C(1)); 1.75–1.55(m, 2H—C(2)); 1.55–1.25 (m, 2H—C(4), 2H—C(5)); 0.93(t, J=6.9, 3H—C(6)).

$^{13}$C-NMR: 71.36(d); 61.21(t); 39.89(t); 38.35(t); 18.76(t); 14.07(q).

MS: 100(15, [M–18]$^+$), 85(8), 75(100), 57(80), 45(50), 43(53).

Heptane-1,3-diol

B.p. 92–94°/2.5 mbar.

$^1$H-NMR (after exchange with D$_2$O): 3.80(m, H—C(3), 2H—C(1)); 1.75–1.25(3m, 8H); 0.91 (t,J=7.1, 3H—C(7)).

$^{13}$C-NMR: 71.58(d); 61.16(t); 38.37(t); 37.43(t); 27.79(t); 22.74(t); 14.07(q).

MS: 114(2, [M–18]$^+$), 85(40), 75(92), 69(45), 57(100), 45(68), 44(54), 41(55).

4-Methylpentane-1,3-diol

B.p. 130–135° C./11 mbar.

$^1$H-NMR (after exchange with D$_2$O): 3.80(m, 2H—C(1)); 3.53(m, H—C(3)); 1.75–1.55(m, 2H—C(2), H—C(4)); 0.93, 0.91(2d, J=6.7, 3H—C(5), Me—C(4)).

$^{13}$C-NMR: 76.60(d); 61.61(t); 35.03(t); 33.98(t); 18.44 (q); 17.71(q).

MS: 100(10, [M–H$_2$O]$^+$), 75(100), 57(95), 45(70), 43(65).

b) General Procedure for the Preparation of the Intermediates (V)

KH dispersion (ca. 35%, 11.80 g, ca. 100 mmol; freed from mineral oil by washing with 3 portions of anhydrous pentane) was suspended in anhydrous THF (200 ml). Diol (IV) (according to Table 2, 100 mmol) in 200 ml of THF was added dropwise. After stirring at room temperature for 90 min, R$^1$I (according to Table 2, 100 mmol) was introduced at a rate such that the internal temperature did not rise above 6–10° (ice water bath). The mixture was stirred at room temperature overnight. THF was partially evaporated under reduced pressure. After work-up (Et$_2$O) and concentration, the crude product was purified by flash chromatography (cyclohexane/Et$_2$O 7:3). The GC homogeneous fractions were combined and distilled (Vigreux column) to give the intermediates (V).

TABLE 2

| R$^2$ | R$^1$ | Final product | Yield |
|---|---|---|---|
| $^n$Pr | Et | 1-Ethoxyhexan-3-ol | 47% |
| $^n$Bu | Me | 1-Methoxyheptan-3-ol | 48% |
| $^n$Bu | Et | 1-Ethoxyheptan-3-ol | 43% |
| $^i$Pr | Me | 1-Methoxy-4-methylpentan-3-ol | 44% |

1-Ethoxyhexan-3-ol

B.p. 91–93°/11 mbar.

$^1$H-NMR: 3.79(m, H—C(3)); 3.68(dt, J=9.5, 5.1, H—C(1)); 3.59(ddd, J=9.5, 4.7, 4.1, H—C(1)); 3.50(q, J=7.1, CH$_2$O); 1.70(m, 2H—C(2)); 1.55–1.30(m, 4H); 1.20(t, J=7.1, CH$_3$CH$_2$)); 0.93(t, J=6.7, 3H—C(6)).

$^{13}$C-NMR: 71.34(d); 69.71(t); 66.61(t); 39.72(t); 36.38(t); 18.81(t); 15.18(q); 14.14(q).

MS: 145(1, [M–1]$^{+)}$, 128(3), 113(3), 103(45), 85(30), 71(16), 59(100), 45(52).

1-Methoxyheptan-3-ol

B.p. 120°/15 mbar.

$^1$H-NMR: 3.77(m, H—C(3)); 3.63(dt, J=9.5, 5.1, H—C(1)); 3.54(ddd, J=9.5, 4.7, 4.1, H—C(1)); 3.35(s, MeO); 2.90(d, J=2.8, OH); 1.70(m, 2H—C(2)); 1.55–1.24(m, 6H); 0.90(t, J=7.1, 3H—C(7)).

$^{13}$C-NMR: 71.78(t); 71.41(d); 58.89(s, MeO); 37.22(t); 36.35(t); 27.82(t); 22.77(t); 14.09(q).

MS: 128(2, [M–18]$^+$), 113(2), 89(86), 71(29), 57(30), 45(100), 41(31).

1-Ethoxyheptan-3-ol

B.p. 101–103°/11 mbar.

¹H-NMR: 3.77(m, H—C(3)); 3.68, 3.59(2m, 2H—C(1)); 3.49(q, J=6.7, CH₂O); 3.19(d, J=2.8, OH); 1.70(m, 2H); 1.55–1.25(6H); 1.20(t, J=6.7, CH₃CH₂); 0.91(t, J=7.1, 3H—C(7)).

¹³C-NMR: 71.69(d); 69.76(t); 66.63(t); 37.24(t); 36.36(t); 27.85(t); 22.79(t); 15.19(q); 14.10(q).

MS: 159(1, [M−1]⁺), 142(4), 127(3), 103(55), 85(29), 72(20), 59(100), 45(55).

1-Methoxy-4-methylpentan-3-ol

B.p. 70–73°/15 mbar.

¹H-NMR: 3.65(dt, J=9.1, 5.2, H—C(1)); 3.55(m, H—C(1), H—C(3)); 3.35(s, MeO); 2.87(d, J=3.2, OH); 1.75–1.60 (m, 2H—C(2), H—C(4)); 0.93, 0.91(2d, J=7.1, 3H—C(5), Me—C(4)).

¹³C-NMR: 76.27(d); 72.13(t); 58.88(q); 33.73(d); 33.10 (t); 18.46(q); 17.69(q).

MS: 133(0.5, [M+1]⁺), 100(5, [M−MeOH]⁺), 89(64), 71(14), 57(16), 45(100).

c) General Procedure for the Preparation of the thio esters (I)

To a solution of 1,3-dimethyl-2-fluoropyridinium 4-methylbenzenesulfonate (4.90 g, 16.5 mmol) in acetone/benzene 1:1 (40 ml), Et₃N was added (2.30 ml, 16.5 mmol), followed by the intermediates (V) (according to Table 3, 15 mmol). The clear solution was stirred for 1 h. Thioacetic acid (1.17 ml, 16.5 mmol) and NEt₃ (2.30 ml, 16.5 mmol) in acetone/benzene 1:1 (5 ml) were added. The mixture was heated at 75° for 3 h. Work-up (Et₂O) and purification of the crude product by flash chromatography (cyclohexane/Et₂O 96:4) afforded, after distillation, the thio esters (I).

TABLE 3

| R² | R¹ | Final product | Yield |
| --- | --- | --- | --- |
| ⁿPr | Et | S-[1-(2-Ethoxyethyl)butyl] ethanethioate | 53% |
| ⁿBu | Me | S-[1-(2-Methoxyethyl)pentyl] ethanethioate | 73% |
| ⁿBu | Et | S-[1-(2-Ethoxyethyl)pentyl] ethanethioate | 60% |
| ⁱPr | Me | S-[1-(2-Methoxyethyl)-2-methylpropyl]ethanethioate | 55% |

S-[1-(2-Ethoxyethyl)butyl] ethanethioate

B.p. 66–68°/0.9 mbar.

IR: 1707 s, 1124 s.

¹H-NMR: 3.63(m, H—C(1)); 3.47(m, CH₂CH₂O); 3.45 (q, J=6.7, CH₃CH₂O); 2.31(s, MeCO); 1.91, 1.79(2m, CH₂—C(1)); 1.58(m, 2H); 1.39(m, 2H); 1.18(t, J=6.7, CH₃CH₂O); 0.90(t, J=7.1, 3H—C(4)).

¹³C-NMR: 195.75(s); 68.08(t); 66.24(t); 41.55(d); 37.36 (t); 34.79(t); 30.75(q); 19.97(t); 15.20(q); 13.87(q).

MS: 206(0.5), 205(1), 204(10, M⁺), 161(100), 128(20), 117(43), 102(15), 99(14), 85(47), 73(37), 59(30), 43(24).

S-[1-(2-Methoxyethyl)pentyl] ethanethioate

B.p. 77°/1 mbar.

IR: 1707 s, 1124s.

¹H—NMR: 3.60(m, H—C(1)); 3.42(m, CH₂O); 3.31(s, MeO); 2.32(s, MeCO); 1.90, 1.79(2m, CH₂—C(1)); 1.60(m, 2H); 1.32(m, 4H); 0.88(t,J=7.1, 3H—C(5)).

¹³C-NMR: 195.7(s); 70.24(t); 58.64(q); 41.67(d); 34.80 (t); 34.68(t); 30.76(q); 28.93(t); 22.50(t); 13.97(q).

MS: 206(0.5), 205(1), 204(3, M⁺), 161(35), 129(22), 114(7), 103(12), 96(18), 71(44), 59(38), 55(49), 45(100), 41(95).

S-[1-(2-Ethoxyethyl)pentyl] ethanethioate

B.p. 72–73°/0.9 mbar.

IR: 1707 s, 1124 s.

¹H-NMR: 3.61(m, H—C(1)); 3.47(m, CH₂O); 3.45(m, MeCH₂O); 2.31(s,MeCO); 1.98–1.24(4m, 8H); 1.19(t, J=6.7, CH₃CH₂); 0.89(t, J=7.1, 3H—C(5)).

¹³C-NMR: 195.74(s); 68.09(t); 66.24(t); 41.75(d); 34.86 (t); 34.76(t); 30.75(q); 28.90(t); 22.51(t); 15.20(q); 13.97(q).

MS: 218(5, M⁺), 200(4), 175(100), 142(20), 131(60), 103(22), 97(35), 85(55), 73(55), 59(54), 43(55).

S-[1-(2-Methoxyethyl)-2-methylpropyl] ethanethioate

B.p. 90°/1 mbar.

¹H-NMR 3.61(dt, J=10.3, 4.1, 1H of CH₂O); 3.50–3.34 (m, H—C(1), 1H of CH₂O); 3.31(s, MeO); 2.39(s, MeCO); 1.93(m, 2H); 1.70(m, 1H); 0.94, 0.92(2d, J=6.9, 3H—C(3), Me-C(2)).

¹³C-NMR: 195.68(s); 70.58(t); 58.70(q); 47.70(d); 32.50 (t); 32.44(d); 30.82(q); 19.87(q); 18.69(q).

MS: 192(0.2), 191(4), 190(8, M⁺), 147(43), 115(20), 88(24), 71(47), 55(50), 45(100), 43(98).

d) General Procedure for the Preparation of the thiols (I)

To a suspension of LiAlH₄ (100 mg, 2.6 mmol) in anhydrous Et₂O (40 ml) was added dropwise the thio ester (I) (according to Table 4, 3.0 mmol) in Et₂O (10 ml) at 5–10°. The mixture was allowed to warm to room temperature and was stirred for 4 h. After hydrolysis with 10% HCl and work-up with Et₂O, the residue was purified by flash chromatography (pentane/Et₂O 96.5:3.5). Bulb-to-bulb distillation afforded the thiol (I).

TABLE 4

| R² | R¹ | Final product | Yield |
| --- | --- | --- | --- |
| ⁿPr | Et | 1-Ethoxyhexane-3-thiol | 90% |
| ⁿBu | Me | 1-Methoxyheptane-3-thiol | 55% |
| ⁱPr | Me | 1-Methoxy-4-methylpentane-3-thiol | 64% |

1-Ethoxyhexane-3-thiol

B.p. 70°/11 mbar.

IR: 2480w, 2440w, 1247s, 1127s.

¹H-NMR: 3.58(m, 2H—C(1)); 3.48(dq, J=1.6, 7.1, CH₂O); 2.95(m, H—C(3)); 1.97(m, 1H); 1.66–1.40(m, 5H); 1.38(d, J=6.7, SH); 1.12(t, J=6.7, CH₃CH₂); 0.92(t, J=7.1, 3H—C(7)).

¹³C-NMR: 68.09(t); 66.27(t); 41.44(t); 38.96(t); 37.69(d); 20.17(t); 15.22(q); 13.77(q).

MS: 163(1), 162(8, M⁺), 128(7), 116(100), 101(14), 99(15), 88(76), 85(80), 59(50), 55(50), 41(23).

1-Methoxyheptane-3-thiol

B.p. 85°/15 mbar.

IR: 2591 vw, 1124 s.

¹H-NMR: 3.54(m, 2H—C(1)); 3.34(s, MeO); 2.93(m, H—C(3)); 1.97(m, 2H); 1.65(m, 2H); 1.49(m, 2H); 1.38(d, J=7.8, SH); 1.33(m, 2H); 0.91(t, J=7.1, 3H—C(7)).

¹³C-NMR: 70.28(t); 58.71(q); 39.02(t); 38.82(t); 37.83 (d); 29.20(t); 22.44(t); 14.02(q).

MS: 164(0.5), 163(1), 162(11, M⁺), 130(10), 128(9), 101(9), 97(15), 88(62), 71(55), 55(49), 45(100), 41(35).

1-Methoxy-4-methylpentane-3-thiol

B.p. 75°/15 mbar.

¹H-NMR 3.55(m, 2H—C(1)) 3.35(s, MeO); 2.90(m, H—C(3)); 1.94, 1.85, 1.60(3m, 2H—C(2), H—C(4)); 1.18 (d, J=7.9, SH); 0.99, 0.92(2d, J=6.7, 3H—C(5), Me-C(4)).

$^{13}$C-NMR: 70.61(t); 58.70(q); 44.27(d); 36.20(t); 33.94 (d); 20.19(q); 17.29(q).

MS: 150(0.5, [M+2]$^+$), 149 (1, [M+1]$^+$), 148(9, M$^+$116 (15), 114(10), 101(5), 88(10), 83(20), 71(35), 67(5), 58(9), 55(30), 47(2), 45(100), 41(24).

EXAMPLE 2

Synthesis of the Optically Active Compounds of the Invention

The compounds of the invention may be prepared by the method summarized in the following scheme II:

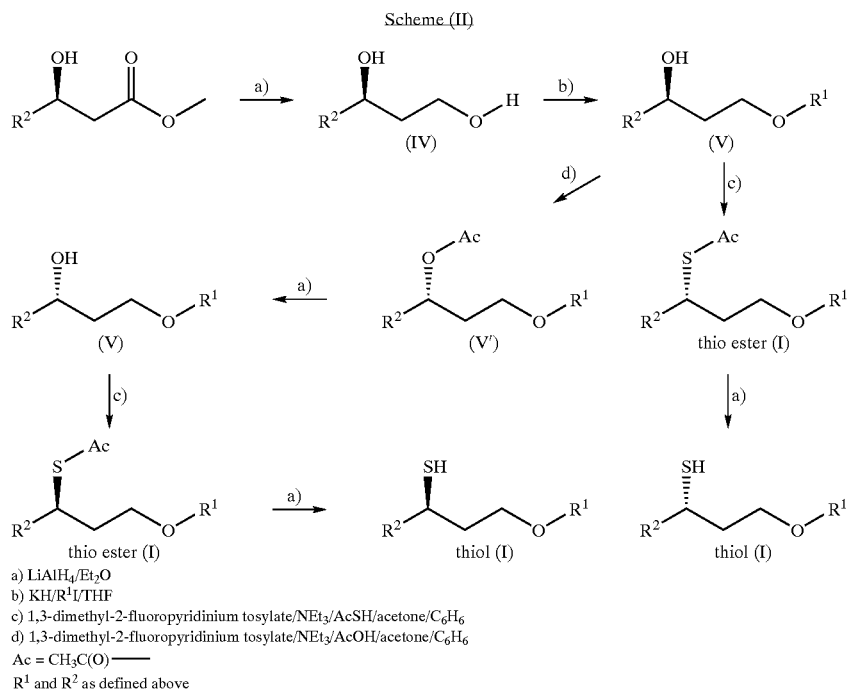

Scheme (II)

a) LiAlH$_4$/Et$_2$O
b) KH/R$^1$I/THF
c) 1,3-dimethyl-2-fluoropyridinium tosylate/NEt$_3$/AcSH/acetone/C$_6$H$_6$
d) 1,3-dimethyl-2-fluoropyridinium tosylate/NEt$_3$/AcOH/acetone/C$_6$H$_6$
Ac = CH$_3$C(O)—
R$^1$ and R$^2$ as defined above The starting optically active alcohol methyl (R)-3-hydroxy-heptanoate was obtained according to the method described by M. Utaka et al. in J.Org.Chem, 1990, 55, 3917. The starting optically active alcohol methyl (S)-3-hydroxy-4-methylpentanoate was obtained according to the method described by N. Mochizuki et al. in Biosci. Biotechnol. Biochem., 1994, 58, 1666.

a) General Procedure for the Preparation of Intermediates (IV)

To a suspention of LiAlH$_4$ (2.91 g, 76 mmol) in anhydrous Et$_2$O (250 ml) was added dropwise at 5–10° the starting compound hydroxy ester (structure according to Table 5, 75 mmol) in 75 mL of Et$_2$O. The reaction mixture was stirred at room temperature overnight. The suspension was cooled to 5° and was carefully hydrolyzed by consecutive addition of water (2.9 ml), 15% NaOH (2.9 ml) and water (8.7 ml). After having been stirred for 40 min at room temperature, solid Na$_2$SO$_4$ was added, and the whole was filtered through a glass frit. The filtrate was concentrated in vacuo to give crude diol intermediates (IV).

TABLE 5

| R$^2$ | Final product | Yield |
|---|---|---|
| $^n$Bu | (R)-heptane-1,3-diol | 99% |
| $^i$Pr | (S)-4-methylpentane-1,3-diol | 81% |

(R)-Heptane-1,3-diol the analytical data are identical to those of the racemic diol and are described in example 1, $[\alpha]_D^{20}=1.0°\pm0.2°(c=1.00, CHCl_3)$ (S)-4-Methylpentane-1,3-diol the analytical data are identical to those of the racemic diol and are described in example 1, $[\alpha]_D^{20}=12.3°(c=1.01, CHCl_3)$ b) General Procedure for the Preparation of the Intermediates (V)

The intermediates (V) were obtained by following the same experimental procedure as described in example 1.b) and using MeI as alkylating agent. The crude product was purified by flash chromatography (cyclohexane/Et$_2$O 7.5:2.5 then 7:3). The GC homogeneous fractions were combined and distilled (Vigreux column) to give the intermediates (V).

TABLE 6

| R$^2$ | R$^1$ | Final product | Yield |
|---|---|---|---|
| $^n$Bu | Me | (R)-1-Methoxyheptan-3-ol | 51.4% |
| $^i$Pr | Me | (S)-1-Methoxy-4-methylpentan-3-ol | 41.5% |

(R)-1-Methoxyheptan-3-ol the analytical data are identical to those of the racemic monoether and are described in example 1, $[\alpha]_D^{20}$32 10.0°(c=1.00, CHCl$_3$)

(S)-1-Methoxy-4-methylpentan-3-ol the analytical data are identical to those of the racemic monoether and are described in example 1, $[\alpha]_D^{20}$=−0.7±0.2°(c=1.01, CHCl$_3$)

c) General Procedure for the Preparation of the Esters (V')

This compound was prepared from (R)-1-methoxyheptan-3-ol via inversion of configuration. The synthesis consists in the LiAlH$_4$ reduction of [(S)-1-(2-methoxyethyl)pentyl] acetate, according to the same procedure as described in example 1.d). [(S)-1-(2-methoxyethyl)pentyl] acetate was obtained by the same procedure as described in example 1.c) but in the presence of acetic acid instead of thioacetic acid.

(S)-1-Methoxyheptan-3-ol the analytical data are identical to those of the racemic monoether and are described in example 1, $[\alpha]_D^{20}$=−9.9(c=1.10, CHCl$_3$)

d) General Procedure for the Preparation of the thio esters (I)

The optically active thio esters (I) were obtained by following the same experimental procedure as described in Example 1.c) and using the corresponding optically active starting material according to scheme (II).

TABLE 7

| R$^2$ | R$^1$ | Final product | Yield |
|---|---|---|---|
| $^n$Bu | Me | (S)-S-[1-(2-Methoxyethyl)pentyl] ethanethioate | 64% |
| $^n$Bu | Me | (R)-S-[1-(2-Methoxyethyl)pentyl] ethanethioate | 60% |
| $^i$Pr | Me | (R)-S-[1-(2-Methoxyethyl)-2-methylpropyl]ethanethioate | 24% |

(S)—S-[1-(2-Methoxyethyl)pentyl] ethanethioate the analytical data are identical to those of the racemic thio ester and are described in example 1, $[\alpha]_D^{20}$=9.4°(c=1.10, CHCl$_3$)

(R)—S-[1-(2-Methoxyethyl)pentyl] ethanethioate the analytical data are identical to those of the racemic thio ester and are described in example 1, $[\alpha]_D^{20}$=−9.2°(c=1.10, CHCl$_3$)

(R)—S-[1-(2-Methoxyethyl)-2-methylpropyl] ethanethioate the analytical data are identical to those of the racemic thio ester and are described in example 1, $[\alpha]_D^{20}$=1.2°(c=0.99, CHCl$_3$)

e) General Procedure for the Preparation of the thiols (I)

The optically active thiol (I) was obtained by following the same experimental procedure as described in Example 1.d) and using the corresponding optically active starting material according to scheme (II).

TABLE 8

| R$^2$ | R$^1$ | Final product | Yield |
|---|---|---|---|
| $^n$Bu | Me | (S)-1-Methoxyheptane-3-thiol | 91% |
| $^n$Bu | Me | (R)-1-Methoxyheptane-3-thiol | 91% |
| $^i$Pr | Me | (R)-1-Methoxy-4-methylpentane-3-thiol | 64% |

(S)-1-Methoxyheptane-3-thiol the analytical data are identical to those of the racemic thio ester and are described in example 1, $[\alpha]_D^{20}$=−0.6±0.2°(c=1.10, CHCl$_3$)

(R)-1-Methoxyheptane-3-thiol the analytical data are identical to those of the racemic thio ester and are described in example 1, $[\alpha]_D^{20}$=0.7±0.2°(c=1.10, CHCl$_3$)

(R)-1-Methoxy-4-methylpentane-3-thiol the analytical data are identical to those of the racemic thio ester and are described in example 1, $[\alpha]_D^{20}$=23.0° (c=1.03, CHCl$_3$)

EXAMPLE 3

Preparation of a Clary Sage Type Perfuming Composition

A composition with a clary-sage type odor, inspired by the main constituents of clary-sage, was prepared by admixing the following ingredients:

| Ingredients | Parts by weight |
|---|---|
| Geranyl acetate | 70 |
| Linalyl acetate | 6500 |
| Neryl acetate | 30 |
| 10%* cis-3-Hexenol acetate | 5 |
| 10%* C9 aldehyde | 1 |
| Camphor | 20 |
| (+)-Carvone | 2 |
| 10%* Cetalox ®$^{1)}$ | 10 |
| Citronellol | 10 |
| 10%* Coumarine | 2 |
| 1%* Damascenone | 20 |
| Dipropylene glycol | 30 |
| Eucalyptol | 30 |
| 10%* Eugenol | 5 |
| Geraniol | 40 |
| Lemongrass | 20 |
| Linalool | 1500 |
| 10%* Menthone | 10 |
| Myroxyde ®$^{2)}$ | 50 |
| Nerol | 20 |
| 10%* Nerol oxide | 20 |
| 10%* Pipol | 15 |
| Terpineol | 80 |
| 10%* Benzyl tiglate | 10 |
| Total | 8500 |

*in dipropylene glycol (DIPG)
$^{1)}$8,12-epoxy-13,14,15,16-tetranorlabdane; origin: Firmenich SA, Geneva, Switzerland
$^{2)}$6,7-epoxy-3,7-dimethyl-octadiene; origin: Firmenich SA, Geneva, Switzerland To this base composition there were added 400 parts of a DIPG solution containing 100 ppm of 1-methoxy-4-methylpentane-3-thiol, or 200 parts of a diethylphthalate solution containing 1000 ppm of 1-methoxy-3-hexanethiol, or respectively 100 parts of a DIPG solution containing 100 ppm of 1-ethoxyhexane-3-thiol and the mixture was completed with dipropylene glycol to obtain a total of 10.000 parts per weight. Three novel compositions were thus obtained which were evaluated on a blind test by a panel of expert perfumers.

The composition containing the 1-methoxy-3-hexanethiol described in EP 0 982 295 presented a clear scent of the clary sage flower type.

On the contrary, the composition containing 1-methoxy-4-methylpentane-3-thiol according to the invention was judged to possess a very distinct fragrance more typical of clary sage seeds and appeared as softer, less sharp and with an enhanced fruity character when compared to the prior art fragrance.

Finally, the composition which contained 1-ethoxyhexane-3-thiol had a less powerful scent than the one containing 1-methoxy-3-hexanethiol, but with a clear blackcurrant note, totally absent from the prior known fragrance.

EXAMPLE 4

Flavoring Composition and Flavored Product Thereof

A flavoring base composition with a berry character was prepared by admixing the following ingredients:

| Ingredients | Parts by weight |
| --- | --- |
| 4-(4-Methoxyphenyl)-2-butanone | 20.00 |
| Ethyl isovalerianoate | 40.00 |
| Maltol | 20.00 |
| Isobutiric acid | 10.00 |
| β-Damascone[1] | 0.10 |
| Ionone beta | 0.30 |
| Ethyl acetate | 50.00 |
| Ethyl butyrate | 20.00 |
| 1%* Bucchu oil | 0.50 |
| Propylene glycol | 839.1 |
|  | 1000 |

*in ethanol
[1] 1-(2,6,6-trimethyl-1-cyclohexen-1-yl)-2-buten-1-one; origin: Firmenich SA, Geneva, Switzerland To a sorbet or a hand boiled candy, obtained as described below, there were added 0.1% by weight or 0.2% by weight, respectively, of the above flavoring composition, to prepare a base composition for comparison.

This base sorbet, or candy, which does not contain any compound according to the invention, was compared to a new sorbet, or candy, containing the above-described flavoring composition and containing also 0.05% by weight of a 0.1% solution in ethanol of (S)-1-methoxyheptane-3-thiol. This composition of the invention was then compared to the base composition, on a blind test.

According to the flavorists, the addition of the compound according to the invention imparted to the sorbet, or candy, a pleasant and typical berry note, with blackcurrant, strawberry, raspberry and blackberry tonalities.

The sorbet was prepared by admixing the following ingredients and using the usual techniques:

| Ingredients | Parts by weight |
| --- | --- |
| Sugar | 150.0 |
| Glucose 40 DE syrup | 40.0 |
| Citric acid | 7.0 |
| Maleic acid | 3.0 |
| Lactic acid | 0.5 |
| Trisodium citrate (20% aqueous solution) | 2.0 |
| Meypyrogen ® IC 304[1] | 3.5 |
| Water | 794.0 |
|  | 1000 |

[1] origin: Meyhall Chemical AG, Kreuzlingen, Switzerland

The candy was prepared by admixing the following ingredients and using the usual mixing techniques:

| Ingredients | Parts by weight |
| --- | --- |
| 65% Glucose syrup | 122.0 |
| Glucose | 30.0 |
| Citric acid | 1.5 |
|  | 153.5 |

What is claimed is:

1. 1-Methoxyheptane-3-thiol in the form of any one of its isomers or of a mixture thereof.

2. As a compound according to claim 1, (S)-1-methoxyheptane-3-thiol.

3. A flavoring composition or a flavored product containing as active ingredient a compound according to claim 1.

4. A flavored product according to claim 3, in the form of a dessert-cream, candy, beverage, soda, juice, compote or fruit jam, yogurt or another dairy product, chewing-gums, pharmaceutical preparations, soup or stock, cube stock, dressing, snack, sauce or a ready cooked dish.

5. A flavoring composition or a flavored product containing as active ingredient a compound according to claim 2.

6. A flavored product according to claim 5, in the form of a dessert, ice-cream, candy, beverage, soda, juice, compote or fruit jam, yogurt or another dairy product, chewing-gums, pharmaceutical preparations, soup or stock, cube stock, dressing, snack, sauce or a ready cooked dish.

7. A method to confer, improve, enhance or modify the flavor properties of a flavor composition or a flavored product, which method comprises adding a compound according to claim 1 flavoring ingredient to said composition or product in an amount sufficient to impart flavor notes reminiscent of berries to the composition or product.

* * * * *

UNITED STATES PATENT AND TRADEMARK OFFICE
CERTIFICATE OF CORRECTION

| | |
|---|---|
| PATENT NO. | : 7,008,919 B2 |
| APPLICATION NO. | : 10/106541 |
| DATED | : March 7, 2006 |
| INVENTOR(S) | : Van De Waal et al. |

Page 1 of 1

It is certified that error appears in the above-identified patent and that said Letters Patent is hereby corrected as shown below:

<u>Column 14</u>:
Line 41 (claim 4, line 2), change "dessert-cream," to -- dessert, ice-cream, --.
Line 56 (claim 7, line 4), after "according to claim 1" insert "as".

Signed and Sealed this

Fifth Day of September, 2006

JON W. DUDAS
*Director of the United States Patent and Trademark Office*